(12) United States Patent
Crooms et al.

(10) Patent No.: US 8,551,043 B2
(45) Date of Patent: Oct. 8, 2013

(54) FEEDING DEVICE AND BOLSTER APPARATUS AND METHOD FOR MAKING THE SAME

(75) Inventors: Dannette Crooms, Sandy, UT (US); Jay Gerondale, Newbury Park, CA (US)

(73) Assignee: C. R. Bard, Inc., Murray Hill, NJ (US)

( * ) Notice: Subject to any disclaimer, the term of this patent is extended or adjusted under 35 U.S.C. 154(b) by 716 days.

(21) Appl. No.: 11/738,979

(22) Filed: Apr. 23, 2007

(65) Prior Publication Data

US 2007/0255209 A1 Nov. 1, 2007

Related U.S. Application Data

(60) Provisional application No. 60/745,310, filed on Apr. 21, 2006.

(51) Int. Cl.
*A61M 29/00* (2006.01)
*A61J 15/00* (2006.01)

(52) U.S. Cl.
USPC ............................................ 604/103; 604/910

(58) Field of Classification Search
USPC ................. 604/96.01, 523, 104, 102.02, 103, 604/103.1, 910
See application file for complete search history.

(56) References Cited

U.S. PATENT DOCUMENTS

| | | |
|---|---|---|
| 1,719,428 A | 7/1929 | Friedman |
| 2,230,226 A | 2/1941 | Auzin |
| 3,111,930 A | 11/1963 | Zipper |
| 3,241,514 A | 3/1966 | Grimland |
| 3,397,699 A | 8/1968 | Kohl |
| 3,543,759 A | 12/1970 | McWhorter |
| 3,915,171 A | 10/1975 | Shermeta |
| 4,016,885 A | 4/1977 | Bruner |
| 4,043,338 A | 8/1977 | Homm et al. |
| 4,134,407 A | 1/1979 | Elam |
| 4,177,815 A | 12/1979 | Patel ............................ 604/103 |
| 4,227,293 A * | 10/1980 | Taylor ............................. 29/447 |
| 4,245,639 A | 1/1981 | La Rosa |
| 4,366,708 A | 1/1983 | Warihashi |
| 4,370,982 A | 2/1983 | Reilly |
| 4,398,542 A | 8/1983 | Cunningham et al. |
| 4,535,757 A | 8/1985 | Webster, Jr. ................... 600/18 |
| 4,583,917 A | 4/1986 | Shah |
| 4,592,747 A | 6/1986 | Pool |
| 4,606,347 A | 8/1986 | Fogarty et al. ................ 606/194 |
| 4,608,965 A | 9/1986 | Anspach, Jr. et al. |
| 4,617,015 A | 10/1986 | Foltz |

(Continued)

FOREIGN PATENT DOCUMENTS

EP 0930083 A2 7/1999
JP 2000-515797 T 11/2000

(Continued)

OTHER PUBLICATIONS

International Search Report and written Opinion; Nov. 11, 2007.

(Continued)

*Primary Examiner* — Kevin C Sirmons
*Assistant Examiner* — Andrew Gilbert
(74) *Attorney, Agent, or Firm* — Rutan & Tucker, LLP

(57) ABSTRACT

A medical device that can be used as a feeding tube to provide nutrition or medication to a patient comprises a catheter, a stiffening tip, and an internal bolster.

9 Claims, 5 Drawing Sheets

(56) References Cited

U.S. PATENT DOCUMENTS

| | | | |
|---|---|---|---|
| 4,666,433 A | 5/1987 | Parks | |
| 4,685,901 A | 8/1987 | Parks | |
| 4,701,163 A | 10/1987 | Parks | |
| 4,729,706 A | 3/1988 | Peterson et al. | |
| 4,744,788 A | 5/1988 | Mercer, Jr. | |
| 4,798,592 A | 1/1989 | Parks | |
| 4,863,438 A | 9/1989 | Gauderer et al. | |
| 4,872,483 A | 10/1989 | Shah | |
| 4,944,732 A | 7/1990 | Russo | |
| 4,994,034 A | 2/1991 | Botich et al. | |
| 5,007,900 A | 4/1991 | Picha et al. | |
| 5,071,405 A | 12/1991 | Piontek et al. | |
| 5,111,310 A | 5/1992 | Parker et al. | |
| 5,112,310 A | 5/1992 | Grobe | |
| 5,163,949 A | 11/1992 | Bonutti | |
| 5,178,423 A | 1/1993 | Combeau | |
| 5,203,773 A | 4/1993 | Green | |
| 5,218,970 A | 6/1993 | Turnbull et al. | |
| 5,234,454 A | 8/1993 | Bangs | |
| 5,248,302 A | 9/1993 | Patrick et al. | |
| 5,255,670 A | 10/1993 | Lomholt | |
| 5,273,529 A | 12/1993 | Idowu | |
| 5,275,610 A | 1/1994 | Eberbach | |
| 5,279,564 A | 1/1994 | Taylor | |
| 5,308,325 A | 5/1994 | Quinn et al. | |
| 5,309,906 A | 5/1994 | LaBombard | |
| 5,324,262 A | 6/1994 | Fischell et al. | |
| 5,342,321 A | 8/1994 | Potter | |
| 5,365,967 A | 11/1994 | Moore | |
| 5,399,173 A | 3/1995 | Parks et al. | 604/533 |
| 5,403,290 A | 4/1995 | Noble | |
| 5,411,491 A | 5/1995 | Goldhardt et al. | |
| 5,429,605 A * | 7/1995 | Richling et al. | 604/103.11 |
| 5,439,444 A | 8/1995 | Andersen et al. | 604/102.02 |
| 5,458,572 A | 10/1995 | Campbell et al. | 604/103.08 |
| 5,458,583 A | 10/1995 | McNeely et al. | |
| 5,462,528 A | 10/1995 | Roewer | |
| 5,462,561 A | 10/1995 | Voda | |
| 5,470,314 A | 11/1995 | Walinsky | 604/103.11 |
| 5,522,961 A | 6/1996 | Leonhardt | 156/252 |
| 5,527,280 A | 6/1996 | Goelz | |
| 5,549,657 A | 8/1996 | Stern et al. | |
| D373,418 S | 9/1996 | Szpak | |
| 5,681,280 A | 10/1997 | Rusk et al. | |
| 5,749,852 A | 5/1998 | Schwab et al. | 604/103.01 |
| 5,836,924 A | 11/1998 | Kelliher et al. | 604/248 |
| 5,860,960 A | 1/1999 | Quinn | |
| 5,910,128 A | 6/1999 | Quinn | |
| 5,935,107 A | 8/1999 | Taylor et al. | |
| 5,941,855 A | 8/1999 | Picha et al. | |
| 5,993,473 A | 11/1999 | Chan et al. | |
| 5,997,503 A * | 12/1999 | Willis et al. | 604/103.07 |
| 5,997,546 A | 12/1999 | Foster et al. | |
| 6,007,243 A | 12/1999 | Ergun et al. | 378/197 |
| 6,033,379 A | 3/2000 | Barra et al. | |
| 6,045,536 A | 4/2000 | Meier et al. | |
| 6,050,987 A | 4/2000 | Rosenbaum | |
| 6,066,155 A | 5/2000 | Amann et al. | 606/192 |
| 6,077,243 A | 6/2000 | Quinn | |
| 6,113,572 A | 9/2000 | Gailey et al. | |
| 6,113,579 A | 9/2000 | Eidenschink et al. | 604/264 |
| 6,149,575 A | 11/2000 | Leonhardt | |
| 6,186,985 B1 | 2/2001 | Snow | |
| 6,221,042 B1 | 4/2001 | Adams | 604/96.01 |
| 6,228,063 B1 | 5/2001 | Aboul-Hosn | |
| 6,264,631 B1 | 7/2001 | Willis et al. | 604/96.01 |
| 6,315,789 B1 | 11/2001 | Cragg | |
| 6,319,244 B2 | 11/2001 | Suresh et al. | 604/525 |
| 6,432,080 B2 | 8/2002 | Pederson, Jr. et al. | 604/103.07 |
| 6,506,179 B1 | 1/2003 | Tiefenthal et al. | 604/103.06 |
| 6,530,898 B1 | 3/2003 | Nimkar et al. | |
| 6,565,536 B1 | 5/2003 | Sohn | |
| 6,582,395 B1 | 6/2003 | Burkett et al. | |
| 6,595,971 B1 | 7/2003 | Von Dyck et al. | 604/334 |
| 6,666,853 B2 | 12/2003 | Chu et al. | |
| 6,669,681 B2 | 12/2003 | Jepson et al. | |
| 6,702,336 B1 | 3/2004 | Chelchowski et al. | |
| 6,705,320 B1 | 3/2004 | Anderson | |
| 6,732,734 B2 | 5/2004 | Ogushi et al. | |
| D490,890 S | 6/2004 | Li | |
| 6,858,019 B2 | 2/2005 | McGuckin, Jr. et al. | |
| 6,878,130 B2 | 4/2005 | Fournie et al. | 604/100.01 |
| 6,896,665 B2 | 5/2005 | Picha et al. | 604/104 |
| 6,916,307 B2 | 7/2005 | Willis et al. | |
| 6,960,222 B2 * | 11/2005 | Vo et al. | 606/200 |
| 6,976,980 B2 | 12/2005 | Brenner et al. | |
| 6,997,909 B2 | 2/2006 | Goldberg | |
| 7,008,438 B2 | 3/2006 | O'Brien | 606/159 |
| 7,041,083 B2 | 5/2006 | Chu et al. | |
| 7,060,050 B2 | 6/2006 | Kliem et al. | 604/96.01 |
| 7,070,587 B2 | 7/2006 | Meier | |
| 7,124,489 B2 | 10/2006 | Triebes et al. | 29/428 |
| 7,186,238 B2 | 3/2007 | Elbert et al. | |
| 7,341,284 B2 | 3/2008 | Mittersteiner et al. | |
| 7,534,224 B2 | 5/2009 | Triebes et al. | |
| 7,547,303 B2 | 6/2009 | DeLegge | |
| 7,582,072 B2 | 9/2009 | McMichael | |
| 7,625,361 B2 | 12/2009 | Suzuki et al. | |
| 7,628,775 B2 | 12/2009 | Adams et al. | |
| 7,819,840 B2 | 10/2010 | Burnside et al. | |
| 8,206,347 B2 | 6/2012 | Burnside et al. | |
| 2002/0093199 A1 | 7/2002 | Le | |
| 2003/0088213 A1 | 5/2003 | Schweikert et al. | |
| 2003/0120260 A1 | 6/2003 | Chu et al. | |
| 2003/0212385 A1 | 11/2003 | Brenner et al. | |
| 2003/0225376 A1 | 12/2003 | Fournie et al. | |
| 2004/0041399 A1 | 3/2004 | Chelchowski et al. | |
| 2004/0103518 A1 | 6/2004 | Triebes et al. | 29/527.2 |
| 2004/0106899 A1* | 6/2004 | McMichael et al. | 604/104 |
| 2004/0106901 A1* | 6/2004 | Letson et al. | 604/104 |
| 2004/0147874 A1* | 7/2004 | Kliem et al. | 604/96.01 |
| 2005/0038381 A1 | 2/2005 | McMichael | 604/96.01 |
| 2005/0200122 A1 | 9/2005 | Mittersteiner et al. | |
| 2005/0267415 A1 | 12/2005 | Jacques | |
| 2006/0276746 A1 | 12/2006 | Burnside et al. | |
| 2007/0021771 A1 | 1/2007 | Oepen et al. | 606/194 |
| 2007/0088259 A1 | 4/2007 | Chu et al. | |
| 2007/0244426 A1 | 10/2007 | Hart et al. | |
| 2007/0276356 A1 | 11/2007 | Downing et al. | |
| 2008/0058730 A1 | 3/2008 | Melsheimer | |
| 2008/0188897 A1 | 8/2008 | Krebs et al. | |
| 2009/0112183 A1 | 4/2009 | Jacques | |
| 2010/0004601 A1 | 1/2010 | Deckard | |
| 2010/0010448 A1 | 1/2010 | Deckard | |
| 2010/0057013 A1 | 3/2010 | Harada | |
| 2010/0185155 A1 | 7/2010 | McMichael et al. | |
| 2010/0312192 A1 | 12/2010 | Fitzgerald et al. | |
| 2011/0196341 A1 | 8/2011 | Howell | |
| 2012/0053485 A1 | 3/2012 | Bloom | |
| 2012/0238959 A1 | 9/2012 | Thorne et al. | |
| 2012/0245519 A1 | 9/2012 | Rotella et al. | |

FOREIGN PATENT DOCUMENTS

| | | |
|---|---|---|
| JP | 4988725 B2 | 8/2012 |
| JP | 2012192182 A | 10/2012 |
| WO | 9819730 A1 | 5/1998 |
| WO | 9852631 A1 | 11/1998 |
| WO | WO02/087492 | 11/2002 |
| WO | 2004050009 A1 | 6/2004 |
| WO | WO 2007/087254 A2 | 8/2007 |
| WO | 2011100310 A2 | 8/2011 |

OTHER PUBLICATIONS

PCT/US2006/022020 filed Jun. 6, 2006 International Preliminary Report on Patentability dated Dec. 6, 2007.

PCT/US2006/022020 filed Jun. 6, 2006 Search Report dated Jan. 25, 2007.

PCT/US2006/022020 filed Jun. 6, 2006 Written Opinion dated Jan. 25, 2007.

U.S. Appl. No. 11/422,559, filed Jun. 6, 2006 Final Office Action dated Apr. 2, 2009.

U.S. Appl. No. 11/422,559, filed Jun. 6, 2006 Non-Final Office Action dated Aug. 8, 2008.

U.S. Appl. No. 11/422,559, filed Jun. 6, 2006 Non-Final Office Action dated Jan. 6, 2010.
U.S. Appl. No. 11/422,559, filed Jun. 6, 2006 Notice of Allowance dated Jun. 24, 2010.
JP 2007-519438 filed Jun. 29, 2005 Decision to Grant dated Sep. 4, 2012.
JP 2007-519438 filed Jun. 29, 2005 Office Action dated Nov. 30, 2010.
Michaud, Laurent et al, Longevity of Balloon-Stabilized Skin-Level Gastrostomy Device, Journal of Pediatric Gastroenterology and Nutrition, 38: 426-429; Apr. 2004.
PCT/US11/24176 filed Feb. 9, 2011 International Preliminary Report on Patentability dated Oct. 11, 2012.
PCT/US11/24176 filed Feb. 9, 2011 International Search Report and Written Opinion dated Jul. 8, 2011.
PCT/US2005/023297 filed Jun. 29, 2005 International Preliminary Report on Patentability dated Jan. 9, 2007.
PCT/US2005/023297 filed Jun. 29, 2005 Search Report dated May 26, 2006.
PCT/US2005/023297 filed Jun. 29, 2005 Written Opinion dated May 26, 2006.
PCT/US2010/041192 filed Jul. 7, 2010 International Search Report dated Sep. 20, 2010.
PCT/US2010/041192 filed Jul. 7, 2010 Written Opinion dated Sep. 20, 2010.
U.S. Appl. No. 11/127,662, filed May 12, 2005 Advisory Action dated May 16, 2008.
U.S. Appl. No. 11/127,662, filed May 12, 2005 Final Office Action dated Mar. 5, 2008.
U.S. Appl. No. 11/127,662, filed May 12, 2005 Final Office Action dated Mar. 6, 2007.
U.S. Appl. No. 11/127,662, filed May 12, 2005 Non-Final Office Action dated Aug. 9, 2007.
U.S. Appl. No. 11/127,662, filed May 12, 2005 Non-Final Office Action dated Jul. 9, 2008.
U.S. Appl. No. 11/127,662, filed May 12, 2005 Non-Final Office Action dated Oct. 17, 2006.
U.S. Appl. No. 11/629,724, filed Jun. 29, 2005 Non-Final Office Action dated Aug. 26, 2008.
U.S. Appl. No. 11/629,724, filed Jun. 29, 2005 Final Office Action dated Jan. 4, 2011.
U.S. Appl. No. 11/629,724, filed Jun. 29, 2005 Final Office Action dated May 4, 2010.
U.S. Appl. No. 11/629,724, filed Jun. 29, 2005 Non-Final Office Action dated Jul. 22, 2010.
U.S. Appl. No. 11/629,724, filed Jun. 29, 2005 Non-Final Office Action dated Oct. 2, 2009.
U.S. Appl. No. 12/265,102, filed Nov. 5, 2008 Advisory Action dated Apr. 3, 2012.
U.S. Appl. No. 12/265,102, filed Nov. 5, 2008 Final Office Action dated Jan. 13, 2012.
U.S. Appl. No. 12/265,102, filed Nov. 5, 2008 Non-Final Office Action dated Dec. 18, 2012.
U.S. Appl. No. 12/265,102, filed Nov. 5, 2008 Non-Final Office Action dated Jul. 29, 2011.
U.S. Appl. No. 12/831,644, filed Jul. 7, 2010 Final Office Action dated Nov. 7, 2012.
U.S. Appl. No. 12/831,644, filed Jul. 7, 2010 Non-Final Office Action dated Mar. 30, 2012.
U.S. Appl. No. 12/902,987, filed Oct. 12, 2010 Final Office Action and Reasons for Allowance dated Dec. 22, 2011.
U.S. Appl. No. 12/902,987, filed Oct. 12, 2010 Notice of Allowance dated Dec. 22, 2011.

* cited by examiner

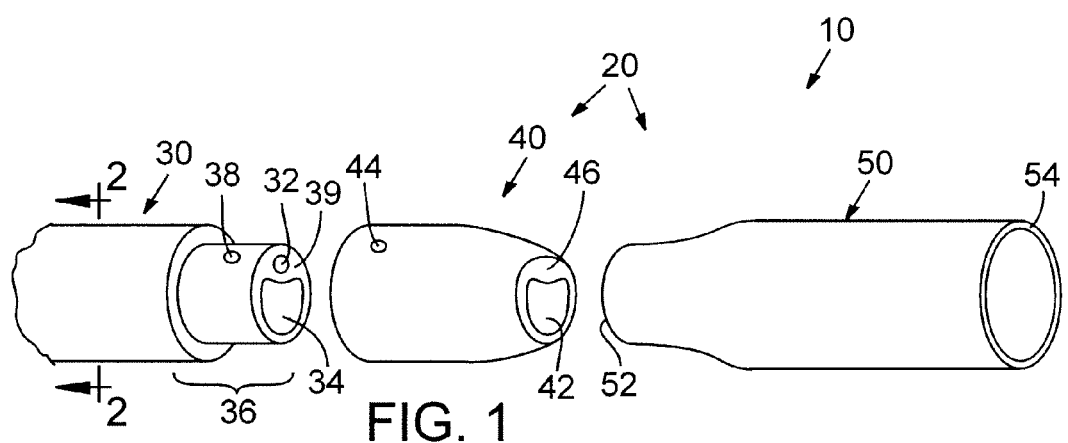
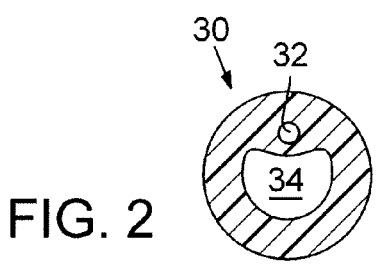

US 8,551,043 B2

FEEDING DEVICE AND BOLSTER APPARATUS AND METHOD FOR MAKING THE SAME

RELATED APPLICATION

This application claims priority to the previously filed provisional Application No. 60/745,310, titled "Feeding Device and Bolster Apparatus" and filed Apr. 21, 2006. This application is incorporated herein by reference in its entirety.

BRIEF DESCRIPTION OF THE DRAWINGS

Advantages of the instant disclosure will become apparent upon review of the following detailed description and drawings, which illustrate representations (not necessarily drawn to scale) of various aspects of the instant disclosure.

FIG. 1 shows an exploded view of a medical device according to one embodiment.

FIG. 2 shows a cross-sectional view of the medical device shown in FIG. 1, along reference line 2-2.

DETAILED DESCRIPTION

With reference to the above-listed drawings, this section describes particular embodiments and their detailed construction and operation. The embodiments described herein are set forth by way of illustration only. Those skilled in the art will recognize in light of the teachings herein that variations can be made to the embodiments described herein and that other embodiments are possible. No attempt is made to exhaustively catalog all possible embodiments and all possible variations of the described embodiments.

For the sake of clarity and conciseness, certain aspects of components or steps of certain embodiments are presented without undue detail where such detail would be apparent to those skilled in the art in light of the teachings herein and/or where such detail would obfuscate an understanding of more pertinent aspects of the embodiments.

Figure 7:
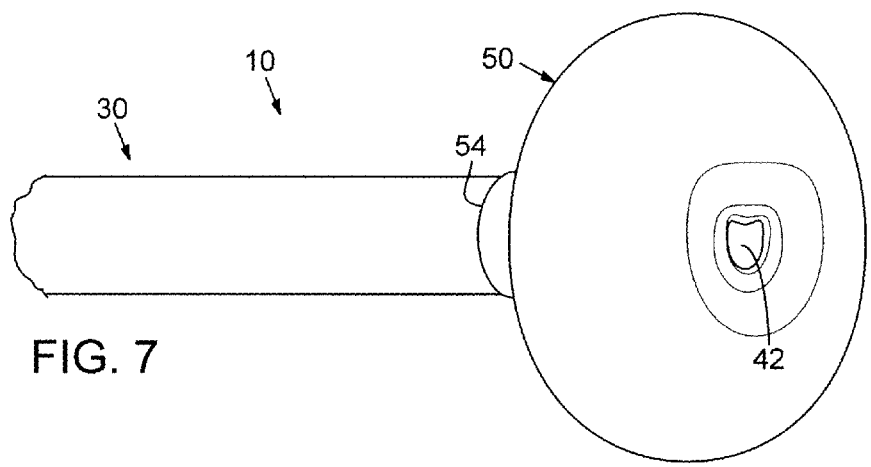
FIG. 7 shows a perspective view of the fully assembled medical device shown in FIG. 5 in an inflated state.
Figure 10:
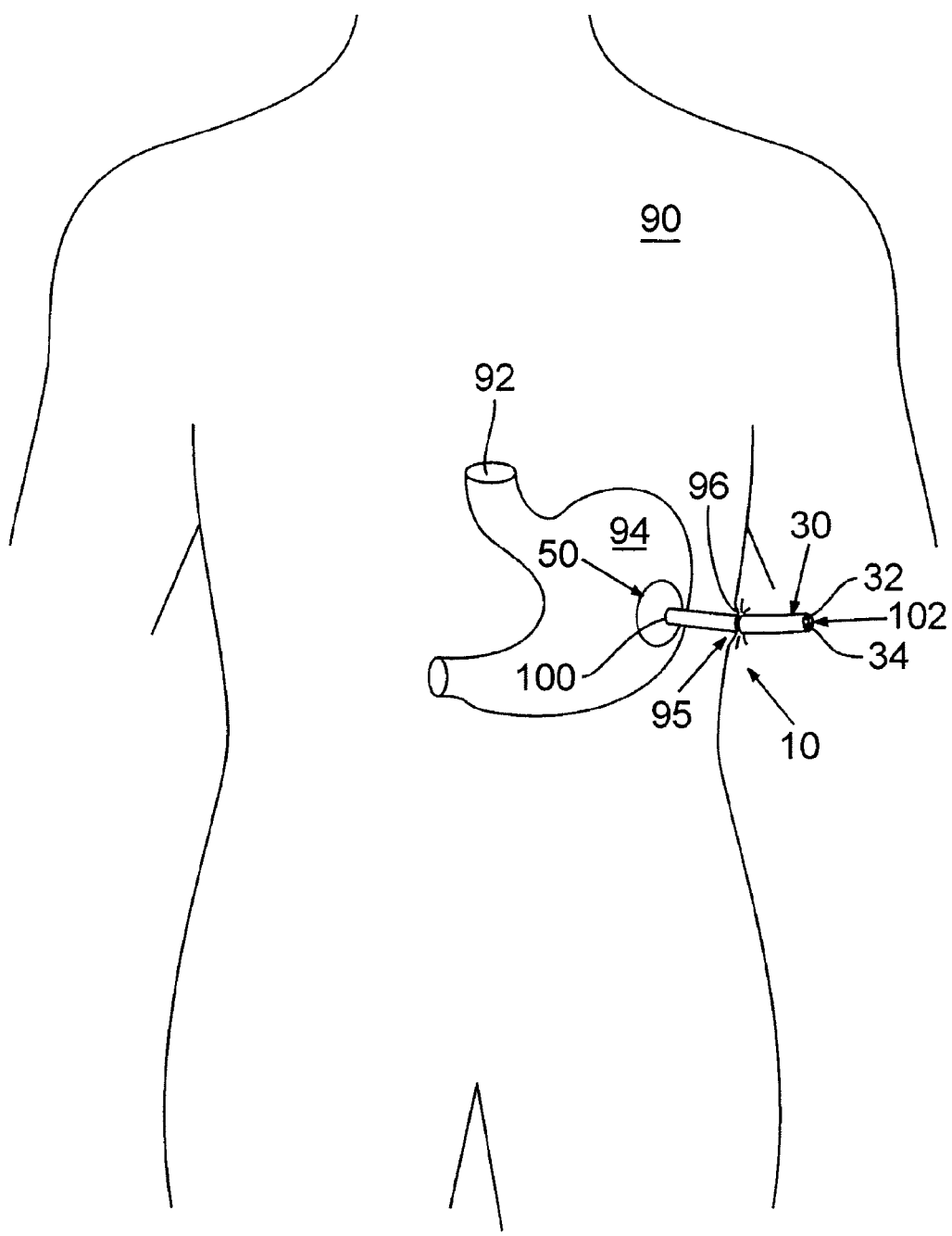
FIG. 10 shows a schematic view of the medical device shown in FIG. 1 positioned within a human body.

FIG. 1 illustrates an exploded view of a medical device 10 that can be used as a feeding tube to provide nutrition and/or medication to a patient who cannot or refuses to swallow. For example, the patient may have a birth defect of the mouth, esophagus, and/or stomach, or have a neuromuscular condition that causes slow eating. The medical device 10 can be temporarily or permanently placed into the gastrointestinal tract (GI tract), such as a stomach 94 (FIG. 10), to administer feeding solutions and/or medications directly into the GI tract. The medical device 10 may include an internal bolster 20 connected to an external feeding adapter via catheter 30. Feeding solutions and medications may be introduced into the feeding adapter (e.g., G-Tube, Low Profile, etc.) to travel through the catheter 30 and internal bolster 20 into the GI tract. Upon inflation, the internal bolster 20 may help secure the medical device 10 in the GI tract (FIGS. 7 and 10).

As shown in FIGS. 1 and 2, the catheter 30 may include a bolster control lumen 32 and an enteral lumen 34. In one embodiment, the bolster control lumen 32 facilitates inflating the internal bolster 20 (FIG. 7) and the enteral lumen 34 facilitates administering feeding solutions and medications to the patient. As shown in FIGS. 1 and 2, the bolster control lumen 32 may be a generally circular inner cavity and the enteral lumen 34 is a generally circular inner cavity having a relief formed to accommodate the bolster control lumen 32. However, the bolster control lumen 32 and the enteral lumen 34 may take different shapes. For example, the enteral lumen 34 may take a more crescent shape to accommodate a larger bolster control lumen or additional lumens. Additionally, the enteral lumen 34 may take a sprocket shape to accommodate a plurality of lumens. As shown, the bolster control lumen 32 has a smaller relative size than the enteral lumen 34. However, the bolster control lumen 32 and enteral lumen 34 may have different relative sizes. In some embodiments, the outside diameter of the catheter 30 falls within the range of 12-28 French (or 4.0 millimeters-9.3 millimeters), but can vary based on the application.

The catheter 30 may be extruded from a biocompatible material, such as silicone or polyurethane. However, the catheter 30 may be made in other ways, such as molding, and include other materials. A tapered tip 36 may be formed on a distal end portion of the catheter 30 (e.g., the end of the catheter 30 that is placed in the GI tract). The tapered tip 36 may be formed by cutting or trimming an external surface of the distal end portion of the catheter 30. Additionally, the tapered tip 36 may be formed during a molding or extruding process. An aperture 38 may be formed in the tapered tip 36. Additionally, the aperture 38 may be formed elsewhere, such as in the distal end portion of the catheter 30, and may be proximate a distal end 39 of the catheter 30. In one embodiment, the aperture 38 intersects the bolster control lumen 32 to provide fluid communication between the bolster control lumen 32 and an inflation chamber 80 (FIG. 8) of the internal bolster 20. The catheter 30 may have reinforcement to help maintain its shape. For example, the catheter 30 may have a wire reinforcement, such as stainless steel or nitinol, within the catheter material. Additionally, one or more concentric rings (made from the same or different material as the catheter) may be formed around the circumference of the catheter 30.

The internal bolster 20 may include a stiffening tip 40 and elongate body 50. The stiffening tip 40 may fit over the elongate body 50 and the tapered tip 36 of the catheter 30 (or simply catheter 30 if the tapered tip 36 is not provided). In one embodiment, the stiffening tip 40 includes a passage 42 sized and shaped to match the enteral lumen 34. However, the passage 42 may take a different shape and may be larger or smaller relative to the enteral lumen 34. An aperture 44 may be formed in the stiffening tip 40 to provide fluid communication between the bolster control lumen 32 and the inflation chamber 80 (FIG. 8) of the internal bolster 20 when aligned with aperture 38. As discussed in more detail with respect to FIG. 9, the apertures 38 and 44 in some embodiments may be preformed in the catheter 30 and stiffening tip 40 or may be machined once the stiffening tip has been attached to the catheter 30.

The external diameter of the stiffening tip may taper proximate the distal end 46 of stiffening tip 40 to facilitate insertion of the catheter 30 into the patient. Additionally, the stiffening tip 40 may be more rigid than the catheter 30. For example, the stiffening tip 40 may have a different hardness than the catheter 30. The stiffening tip 40 may be made from the same or a different material as the catheter 30. Additionally, the stiffening tip 40 may contain a radiopaque material to ensure that the stiffening tip 40 is visible during imaging, such as in X-ray photographs and under fluoroscopy. In one embodiment, an internal diameter of the passage 42 and the enteral lumen 34 remain constant upon inflation. This may help ensure that the feeding solutions and medications will not be obstructed while traveling from the enteral lumen 34 into the GI tract via the passage 42. In some embodiments, the outside diameter of the stiffening tip 40 matches the outside diameter of the catheter 30, but may be larger or smaller based on the application. Additionally, while in one embodiment, the length of the stiffening tip 40 is approximately 0.5 inches (1.27 cm), the length may vary based upon the application.

Figure 8:
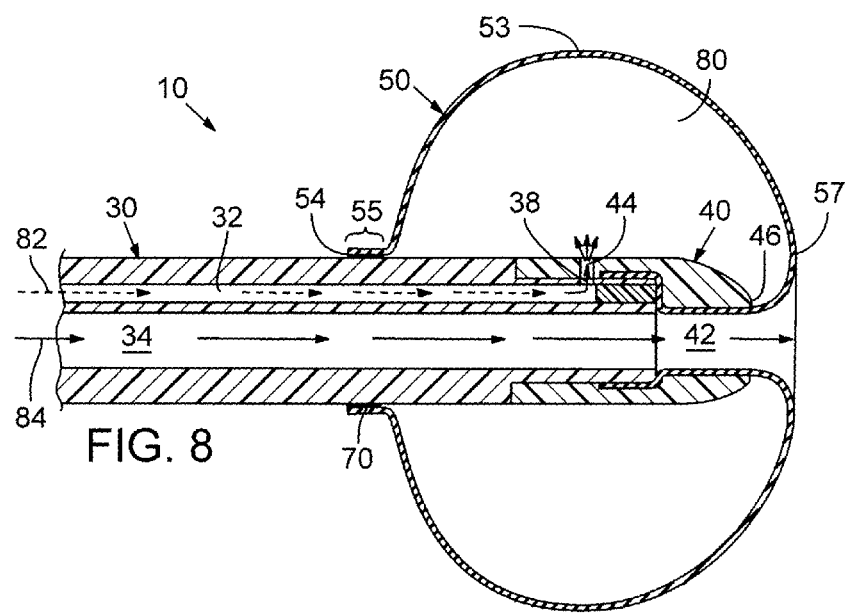
FIG. 8 shows a longitudinal cross-sectional view of the medical device shown in FIG. 7.

The elongate body 50 may be extruded from a biocompatible material, such as silicone or polyurethane, to form a cylindrical balloon having a hollow interior. However, the elongate body 50 may be made in other ways, such as molding, and include other materials. In one embodiment, the elongate body 50 is made from a material that is more elastic than the catheter 30 and the stiffening tip 40 so that the elongate body 50 may be inflated. The elongate body 50 may be sized to fit over the outer diameter of the catheter 30. For example, a proximal end 52 of the elongate body 50 may be sized to fit over the tapered tip 36 of the catheter 30 (or the catheter 30 if the tapered tip 36 is not provided). However, the proximal end 52 of the elongate body 50 may be tapered so that as it is stretched to fit over the catheter 30 a friction fit is formed between the elongate body 50 and catheter 30. As described in more detail with respect to FIGS. 3-6, a distal end 54 of the elongate body 50 may be folded back over the stiffening tip and secured to form an inflation chamber 80 (FIG. 8).

The elongate body 50 may be made from the same or a different material as the catheter 30 and/or stiffening tip 40. Additionally, the elongate body 50 may have a different hardness than the catheter 30 and/or stiffening tip 40 to enhance inflation properties. One or more concentric rings (made from the same or different material as the elongate body 50) may be formed around the circumference of the elongate body 50. This may strengthen the elongate body 50 and may also control the shape of the inflated elongate body 50. While in one embodiment the length of the elongate body 50 is approximately 1.5 inches (3.81 cm), the length may vary based upon the application.

A feeding adapter or coupling may be attached to the proximal end of the catheter 30. The feeding adapter may have a first opening in fluid communication with the bolster control lumen 32. The first opening allows the user, such as a physician or nurse, to selectively control inflation and deflation of the internal bolster 20. Additionally, the feeding adapter may have a second opening in fluid communication with the enteral lumen 34. The second opening allows the feeding solution and/or medication to be injected into the patient. A plug may be provided to seal the second opening and prevent contamination of the catheter 30 when not in use. Additionally, a valve may be provided in the first opening, the second opening, or both, to prevent backflow.

Figure 3:
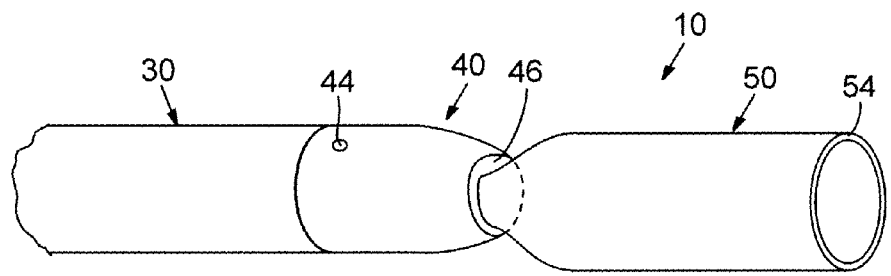
FIG. 3 shows a perspective view of the medical device shown in FIG. 1 partially assembled.
Figure 4:
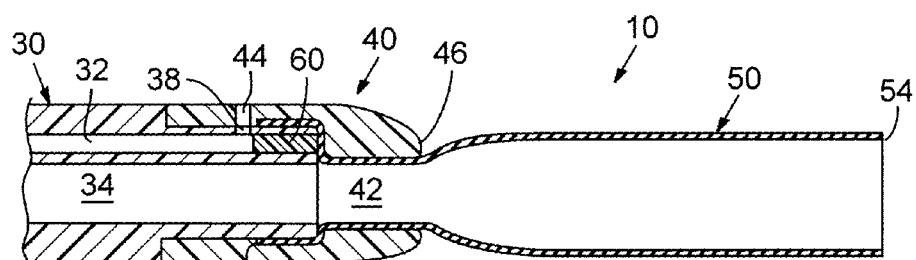
FIG. 4 shows a longitudinal cross-sectional view of the medical device shown in FIG. 3.

Referring now to FIGS. 3 and 4, the medical device 10 is shown partially assembled. The proximal end 52 of the elongate body 50 may be interposed between the distal end of the catheter 30 and the stiffening tip 40. For example, the proximal end 52 of the elongate body 50 may fit over the tapered tip 36 of the catheter 30. As the stiffening tip 40 is slid over the elongate body 50 and secured to the catheter 30, the proximal end 52 of the elongate body 50 may be pinned therebetween. In this embodiment, the stiffening tip 40 may reinforce the bond of the proximal end 52 of the elongate body 50 to the distal end of the catheter 30. By way of another example, the proximal end 52 of the elongate body 50 may extend through the passage 42 of the stiffening tip 40 such that the proximal end 52 is pinned between the distal end 39 of the catheter 30 and the stiffening tip 40.

In one embodiment, the bolster control lumen 32 is occluded by plug 60 (or otherwise occluded or sealed) proximate the distal end 39 of the catheter 30. The elongate body 50 may be nested in an annular recess formed in the stiffening tip 40. By way of example, the recess may be formed from the distal end 46 to the aperture 44. The recess may be deeper than the thickness of the elongate body 50 so that the internal diameter of the enteral lumen 34 and the passage 42 are equal to help prevent clogging. Additionally, the internal diameter of the stiffening tip 40 may be slightly larger near the distal end 46 to accommodate the elongate body 50.

Figure 5:
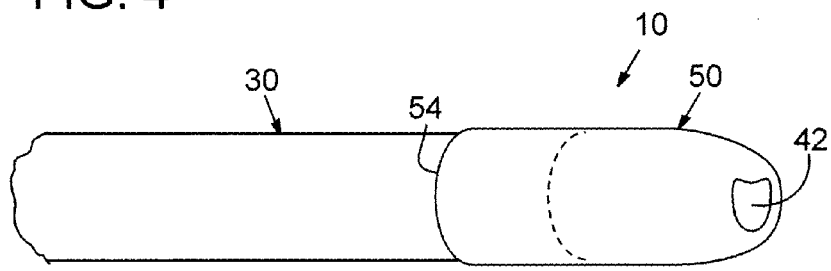
FIG. 5 shows a perspective view of the medical device shown in FIG. 1 fully assembled.
Figure 6:
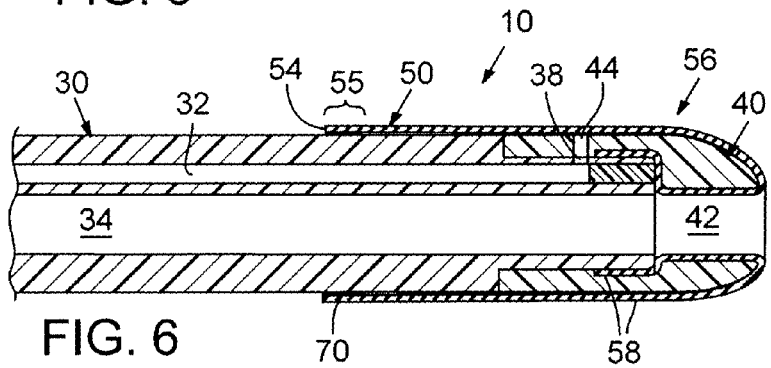
FIG. 6 shows a longitudinal cross-sectional view of the medical device shown in FIG. 5.

Referring now to FIGS. 5 and 6, the medical device 10 is shown fully assembled. A distal end portion of the elongate body 50 may be folded upon itself to define an overfolded end portion 56. The distal end 46 of the stiffening tip 40 may then be interposed between overlapping portions 58 of the overfolded end portion 56. As described in more detail with respect to FIG. 9, the distal end 54 of the elongate body 50 may be folded back over the distal end 46 of the stiffening tip 40 so that a portion of the elongate body 50 extends longitudinally along the catheter 30 and is coaxial therewith. The distal end 54 may then be bonded to a bonding site 70, such as with glue or epoxy, to define the inflation chamber 80 (FIG. 8).

The bonding site 70 may be located between the distal end 39 of the catheter 30 and the proximal end of the catheter 30. For example, the bonding site 70 may be located on an exterior surface of the catheter 30. By way of another example, the bonding site 70 may be located on an exterior surface of the stiffening tip 40. In one embodiment, the bonding site 70 extends approximately 0.5 inches (1.27 cm) along the length of the catheter 30 to define a cuff 55. However, the cuff 55 may have different lengths depending on the application.

In one embodiment, the inflation chamber 80 (FIG. 8) is in fluid communication with the bolster control lumen 32 such that internal bolster 20 distends radially upon inflation (FIG. 7). As previously described, the aperture 44 in the stiffening tip 40 is aligned with the aperture 38 in the catheter 30. This provides a channel through the catheter 30 and the stiffening tip 40 connecting the bolster control lumen 32 with the inflation chamber 80. The channel may be provided in other locations. For example, the channel may be provided proximate the bonding site 70. By way of another example, the channel may be provided through the distal end 46 of the stiffening tip 40. Additionally, more than one channel may be provided to facilitate inflation and deflation of the internal bolster.

Referring now to FIGS. 7 and 8, the medical device 10 is shown inflated. Once the feeding adapter or coupling has been coupled to the catheter 30, the internal bolster 20 may be expanded or inflated as follows. A syringe may be attached to a bolster valve so that the syringe is in fluid communication with the bolster control lumen 32. A plunger may be operated for introducing or removing air, liquid (e.g., a saline solution), or both from the bolster control lumen 32 and the internal bolster 20. For example, the syringe may be operated to transfer a selected amount of gas or liquid 82 to an inflation chamber 80 of the internal bolster 20 via the bolster control lumen 32 and apertures 38 and 44. An inflation pressure generated by the syringe forces the gas or liquid 80 to distend an inflatable portion 53 of the elongate body 50 radially relative to the catheter 30.

In one embodiment, as the internal bolster 20 is inflated an extended portion 57 of the elongate body 50 extends a distance distally before arching proximally toward the cuff 55. This may generate a somewhat donut shape that helps avoid irritation of soft tissue by the stiffening tip 40. The distance the extended portion 57 extends beyond the distal end 46 of the stiffening tip 40 may depend on a number of factors, such as the flexibility and elasticity of the material used to make the elongate body 50 and whether any supports are provided (e.g., concentric rings). Subsequent to expansion of the internal bolster 140, the syringe may be removed from the bolster valve.

As previously described, the stiffening tip 40 may be configured such that the internal diameter of the passage 42 and the internal diameter of the enteral lumen 34 remain constant upon inflation. This may help ensure that the medications and feeding solutions will not be obstructed while traveling from the enteral lumen 34 into the GI tract via the passage 42.

Figure 9:
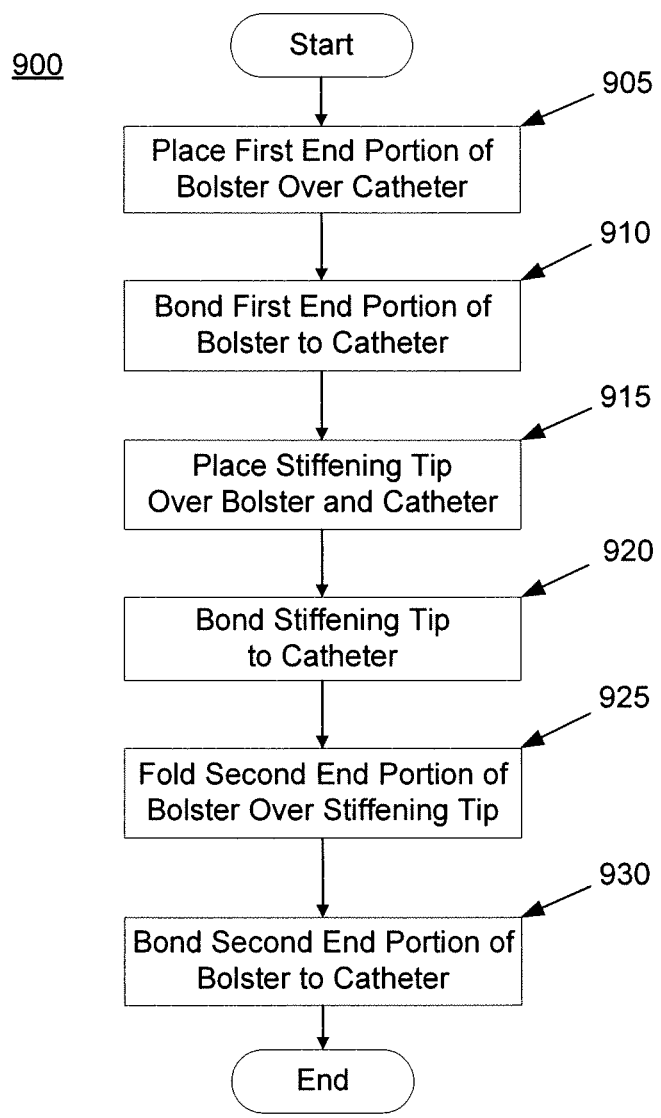
FIG. 9 shows a flow chart for a method of constructing an internal bolster, according to one embodiment.

Referring now to FIG. 9, a method 900 of constructing the medical device 10 will be described according to one embodiment. As previously discussed, the catheter 30 may be extruded from a biocompatible material, such as silicone or polyurethane, or may be molded. The tapered tip 36 may be formed on a distal end portion of the catheter 30, such as by cutting or trimming an external surface of the distal end portion of the catheter 30 or the tapered tip 36 may be formed during the molding or extruding process. Additionally, the bolster control lumen 32 and the enteral lumen 34 may be formed during the molding or extruding process, or may be machined afterwards.

At step 905, a first end portion of the internal bolster 20 may be placed over the catheter 30. For example, the proximal end 52 may be placed over the tapered tip 36 (or the distal end portion of the catheter 30 if the tapered tip 36 is not provided). At step 910, the internal bolster 20 may be bonded to the distal end portion of the catheter 30. For example, the proximal end 52 of the elongate body 50 may be bonded to the catheter 30 with glue or epoxy. By way of another example, the proximal end 52 may be bonded to the catheter 30 during a molding process. Additionally, a mechanical fastener, such as a retaining ring, may be placed over the elongate body 50. In another embodiment, the proximal end 52 of the elongate body 50 is bonded to the stiffening tip 40.

At step 915, the stiffening tip 40 may be placed over the internal bolster 20 and the distal end portion of the catheter 30 such that a portion of the internal bolster 20 extends distally beyond the distal end 46 of the stiffening tip 40 (FIGS. 3 and 4). For example, the elongate body 50 may be passed through the passage 42 of the stiffening tip 40. In doing so, the diameter of the elongate body 50 may decrease to accommodate the passage 42.

The enteral lumen 34 may be aligned with the passage 42 so that the path through the enteral lumen 34 is free from obstructions. Additionally, the aperture 44 in the stiffening tip 40 may be aligned with the aperture 38 in the catheter 30 so that the inflation chamber 80 is in fluid communication with the bolster control lumen 32. In another embodiment, an aperture may be formed or machined in the stiffening tip 40 and the distal end portion of the catheter 30 to provide fluid communication between the inflation chamber 80 and the bolster control lumen 32. Additionally, one or more apertures may be formed elsewhere, such as in the distal end of the catheter between the bonding site 70 and the distal end 39 of the catheter 30.

At step 920, the stiffening tip 40 may be bonded to the distal end portion of the catheter 30, such as with glue or epoxy. In another embodiment, the stiffening tip 40 may be molded over the elongate body 50 and the distal end of the catheter 30. Additionally, a mechanical fastener, such as a retaining ring, may be placed over the stiffening tip 40 to create a friction fit.

At step 925, the distal end 54 of the elongate body 50 may be folded back over the distal end 46 of the stiffening tip 40 and the distal end portion of the catheter 30 to the bonding site 70. As previously discussed, the bonding site 70 may be located between the distal end portion of the catheter 30 and the proximal end of the catheter 30. The bonding site 70 may be located on the exterior surface of the catheter 30 so that the distal end 54 of the elongate body 50 may be bonded to the catheter 30. Additionally, the bonding site 70 may be located on the exterior surface of the stiffening tip 40 so that the distal end 54 of the elongate body 50 may be bonded to the stiffening tip 40.

At step 930, the distal end 54 of the elongate body 50 may be bonded (such as with glue or epoxy) to the catheter 30 or stiffening tip 40 at the bonding site 70 to create the cuff 55. Additionally, the distal end 54 of the elongate body 50 may be molded onto the catheter 30 or stiffening tip 40 at the bonding site 70 or a mechanical fastener, such as a retaining ring, may be placed over the distal end 54 of the elongate body 50 to create a friction fit. An inflation chamber 80 in fluid communication with the bolster control lumen 32 may be defined by the bonding site 70, the inflatable portion 53 of the elongate body 50, the extended portion 57 of the elongate body 50, and the distal end of the catheter 30.

Referring now to FIG. 10, the medical device 10 is positioned within patient 90 via a surgical procedure known in the art, such as gastrostomy. A stoma 95 may be surgically created in the patient's abdomen. For example, a endoscope may be inserted via the patient's mouth. Once the endoscope reaches the patient's stomach 94 a light on the endoscope may shine through the patient's skin so a surgeon can see where to make an incision. The surgeon may then attach the stomach 94 to the patient's abdominal wall. The medical device 10, may then be fitted into the stoma 95 and held in place with the inflated internal bolster 20.

In another embodiment, the medical device 10 may be positioned within the patient 90 via the patient's esophagus 92. The medical device 10 may exit the body through the stoma 95. Thus, a fistula between the stomach 94 and the exterior of a patient's body may be formed by a fistulous lumen of catheter 30. In further detail, catheter 30, and more particularly the fistulous lumen thereof, may form a passage between the stomach 94 and the abdominal surface 96 via distal opening 100 and proximal opening 102 of the enteral lumen 34. The internal bolster 20 and an external bolster may be positioned against the stomach wall and the abdominal surface 96, respectively. The internal bolster 20 and the external bolster may be structured for retaining the medical device 10 within the patient 90. The medical device 10 may also include an anti-reflux valve and a plug to seal proximal opening 102 when the medical device 10 is not being used as a conduit for communicating nutrients or medication to the stomach 94 of the patient 90.

During initial placement or implantation of the medical device 10 (i.e., not replacing another feeding tube device), the details of the endoscopic placement procedure may encompass any such procedures as known in the art. For example, for ease of movement down the esophagus 92, the internal bolster 20, if at least partially inflated or expanded, may be elongated or otherwise deformed (e.g., by using a stylet or other deformation mechanism) as known in the art. Once the medical device 10 is suitably placed and the internal bolster 20 is positioned at a selected location along the stomach wall, the internal bolster 20 may be returned to its original (i.e., not deformed) shape (e.g., by removing the stylet). In another embodiment, the medical device 10 may be endoscopically placed with the internal bolster 20 in a deflated state. Once the internal bolster 20 is positioned at a selected location along the stomach wall, the internal bolster 20 may be inflated or expanded by communicating fluid (e.g., sterile saline) into the internal bolster 20 via the bolster control lumen 32.

The terms and descriptions used herein are set forth by way of illustration only and are not meant as limitations. Those skilled in the art will recognize that many variations can be made to the details of the above-described embodiments without departing from the underlying principles of the invention. The scope of the invention should therefore be determined only by the following claims (and their equivalents) in which all terms are to be understood in their broadest reasonable sense unless otherwise indicated.

What is claimed is:

1. An internal bolster assembly for attachment to a catheter including a bolster control lumen and an enteral lumen, the internal bolster comprising:
    a stiffening tip including a passage formed therein, the stiffening tip attached to a distal end portion of the catheter so that the passage is at least partially aligned with the enteral lumen, an outer diameter of the stiffening tip matching an outer diameter of the catheter where attached; and
    an elongate body including:
        a first end portion extending through a portion of the passage such that a first end of the elongate body is interposed within the passage between the distal end portion of the catheter and the stiffening tip when the stiffening tip is attached to the catheter such that the first end of the elongate body is held in place by the distal end portion of the catheter and the stiffening tip,
        a second end portion for attachment to a bonding site, the bonding site being located between a distal end of the stiffening tip and a proximal end of the catheter, and
        an inflatable portion extending entirely from the distal end of the stiffening tip to the bonding site to define an inflation chamber, the inflation chamber being configured to be in fluid communication with the bolster control lumen of the catheter so that the inflatable portion distends in response to an inflation pressure delivered by the bolster control lumen.

2. The internal bolster assembly of claim 1 wherein the first end portion of the elongate body overlays the distal end portion of the catheter and is attached thereto.

3. The internal bolster assembly of claim 1 wherein an aperture is formed in the stiffening tip and the distal end portion of the catheter to provide the fluid communication between the inflation chamber and the bolster control lumen.

4. The internal bolster assembly of claim 1 wherein the first end portion is folded upon itself to define an overfolded end portion and the stiffening tip is interposed between the overlapping portions of the overfolded end portion and wherein the overfold portion includes an angled portion interposed between the distal end portion of the catheter and the stiffening tip.

5. The internal bolster assembly of claim 1 wherein the inflatable portion distends beyond the distal end of the stiffening tip upon inflation such that the inflatable portion extends a distance distally before arching proximally.

6. The internal bolster assembly of claim 1 wherein the stiffening tip is configured such that an internal diameter of the passage and an internal diameter of the enteral lumen remain constant upon inflation.

7. The internal bolster of assembly claim 1 wherein the stiffening tip is more rigid than the catheter.

8. The internal bolster of assembly claim 1 wherein the stiffening tip includes a radiopaque material, wherein the catheter further comprises wire reinforcement, and wherein the inflatable portion further comprises one or more concentric rings.

9. The internal bolster assembly of claim 1, wherein the first end of the elongated body is sandwiched between the distal end portion of the catheter and the stiffening tip and wherein the bolster control lumen is occluded by a plug.

* * * * *